US008784904B2

(12) United States Patent
Minatelli et al.

(10) Patent No.: US 8,784,904 B2
(45) Date of Patent: Jul. 22, 2014

(54) PLANT DERIVED SEED EXTRACT RICH IN ESSENTIAL FATTY ACIDS DERIVED FROM PERILLA SEED: COMPOSITION OF MATTER, MANUFACTURING PROCESS AND USE

(75) Inventors: John A. Minatelli, Mt. Dora, FL (US); W. Stephen Hill, Ocala, FL (US); Rudi E. Moerck, Sanford, FL (US); Uy Nguyen, Eustis, FL (US)

(73) Assignee: U.S. Nutraceuticals, LLC, Eustis, FL (US)

( * ) Notice: Subject to any disclaimer, the term of this patent is extended or adjusted under 35 U.S.C. 154(b) by 198 days.

(21) Appl. No.: 13/231,131

(22) Filed: Sep. 13, 2011

(65) Prior Publication Data

US 2012/0027787 A1 Feb. 2, 2012

Related U.S. Application Data

(63) Continuation-in-part of application No. 12/419,321, filed on Apr. 7, 2009, now Pat. No. 8,586,104.

(60) Provisional application No. 61/043,773, filed on Apr. 10, 2008.

(51) Int. Cl.
*A61K 36/00* (2006.01)

(52) U.S. Cl.
USPC .......................................... 424/725; 424/776

(58) Field of Classification Search
None
See application file for complete search history.

(56) References Cited

U.S. PATENT DOCUMENTS

| | | | | |
|---|---|---|---|---|
| 5,332,803 | A | 7/1994 | Miyazaki et al. | 530/375 |
| 5,585,400 | A * | 12/1996 | Cook et al. | 514/560 |
| 6,123,965 | A | 9/2000 | Jacob et al. | 424/489 |
| 6,552,081 | B1 * | 4/2003 | Freedman et al. | 514/560 |
| 6,827,965 | B1 | 12/2004 | Fitzpatrick | 426/615 |
| 7,959,950 | B2 | 6/2011 | Evans et al. | 424/489 |
| 2002/0155182 | A1 | 10/2002 | Belna | 424/746 |
| 2002/0168431 | A1 | 11/2002 | Belna | 424/746 |
| 2003/0175403 | A1 | 9/2003 | Gurin | 426/607 |
| 2004/0137132 | A1 | 7/2004 | Nunez et al. | 426/622 |
| 2004/0185129 | A1 | 9/2004 | Vuksan | 424/776 |
| 2006/0127505 | A1 * | 6/2006 | Haines et al. | 424/729 |
| 2006/0147564 | A1 * | 7/2006 | Kim | 424/750 |
| 2007/0266774 | A1 * | 11/2007 | Gibson et al. | 73/53.01 |
| 2008/0095881 | A1 | 4/2008 | Ber | 426/2 |
| 2008/0305096 | A1 | 12/2008 | Verdegem et al. | 424/94.4 |
| 2008/0305190 | A1 | 12/2008 | Vuksan | 424/746 |
| 2009/0048339 | A1 * | 2/2009 | Kanwar et al. | 514/560 |
| 2009/0181127 | A1 | 7/2009 | Minatelli et al. | 426/63 |
| 2009/0258081 | A1 | 10/2009 | Minatelli et al. | 424/523 |
| 2010/0144878 | A1 | 6/2010 | Popp | 514/560 |
| 2010/0216885 | A1 | 8/2010 | Kabaradjian | 514/560 |
| 2010/0260893 | A1 | 10/2010 | Kabaradjian | 426/72 |

FOREIGN PATENT DOCUMENTS

| | | | | |
|---|---|---|---|---|
| CN | 1583009 | * | 2/2005 | |
| DE | 10008948 | | 8/2001 | |
| JP | 63190816 | | 8/1988 | |
| WO | 99/62356 | | 9/1999 | ............. A23K 1/175 |
| WO | 02/072119 | | 9/2002 | ............. A61K 35/78 |
| WO | 2004/022725 | | 3/2004 | |
| WO | 2009126798 | | 10/2009 | |

OTHER PUBLICATIONS

DW 2001-280848, Apr. 2001, Derwent, Bland et al.*
Shin et al., "Lipid composition of perilla seed", Journal of the American Oil Chemists, vol. 71, No. 6, Jan. 1994, pp. 619-622.
Asif, "Health effects of omega-3,6,9 fatty acids: perilla frutescens is a good example of plant oils", Oriental Pharmacy & Experimental Medicine, vol. 11, No. 1, Mar. 2011, pp. 51-59.
Przybylski, "Flax oil and high linelenic oils", Bailey's Industrial Oil and Fat Products, Jan. 2005, pp. 281-301.
Life Extension Magazine, "Perilla oil a source of heart-healthy alpha-linolenic acid", Jan. 2004, pp. 1-4.
Database GNPD, "Entrox dietary supplement", Aug. 2001, p. 1.
Asif, "Nutritional and functional characterisation of perilla frutescens seed oil and evaluation of its effect on gastrointestinal motility". Malaysian Journal of Pharmaceutical Sciences, Jan. 2010, pp. 1-12.
Flavex Naturextrakte (CO2 Extracts, Parfums Cosmetiques Actualities, 2007, 193, Feb./ Mar. 2007, English Abstract, 1 page.
Viable Herbal Solutions (www.web.archive.org/web/20000124113842/http:/viable-herbal.com/herbology 1/herbs42htm, Copyrighted 1996, 1997, 1998 and 2000), pp. 1-3.
"Valensa Introduces Tresalbio™ Salvia Hispanica Seed CO2 Extract," Oct. 9, 2006, Retrieved from the Internet: http://www.usnutra.com/resources/news/Seed-CO2.php, 2 pages.
Coates et al., "Commercial Production of Chia in Northwestern Argentina," Journal of the American Oil Chemists' Society, vol. 75, No. 10, 1998, pp. 1417-1420.
"Valensa Launches O2B™ Peroxidation Blocker Technology at Vitafoods 2006," Jun. 8, 2006, Retrieved from the Internet: http://www.usnutra.com/resources/news/Technologv-Vitafoods.php, 1 page.
Surette et al., "Inhibition of Leukotriene Synthesis, Pharmacokinetics, and Tolerability of a Novel Dietary Fatty Acid Formulation in Healthy Adult Subjects," Clinical Therapeutics, vol. 25, No. 3, Mar. 2003, pp. 948-971.
Reverchon et al., "Supercritical Fluid Extraction and Fractionation of Natural Matter," Journal of Supercritical Fluids, vol. 38, No. 2, Sep. 1, 2006, pp. 146-166.
Illes et al., "Extraction of Hiprose Fruit by Supercritical CO2 and Propane," Journal of Supercritical Fluids, vol. 10, No. 3, Aug. 1, 1997, pp. 209-218.

(Continued)

*Primary Examiner* — Terry A McKelvey
*Assistant Examiner* — Randall Winston
(74) *Attorney, Agent, or Firm* — Allen, Dyer, Doppelt, Milbrath & Gilchrist, P.A.

(57) ABSTRACT

A composition of matter comprises a shelf stable, super critical, $CO^2$ fluid extracted seed oil derived from a cracked biomass of *perilla frutescens*, the seed oil comprising from about 60 to about 95 percent w/w of PUFAs in a ratio of from about 4:1 to about 6:1 alpha-linolenic acid (ALA) to linoleic acid (LA) and a mixture of selected antioxidants.

21 Claims, 2 Drawing Sheets

(56) References Cited

OTHER PUBLICATIONS

Catchpole et al., "*Extraction of Seed Oils Using Supercritical CO2 and Subcritical Propane*," Proceedings of the 2nd International Meeting on High Pressure, 2001, pp. 1-13.

Taga et al., "*Chia Seeds as a Source of Natural Lipid Antioxidants*," Journal of the American Oil Chemists' Society, 1984 Department of Foods and Nutrition, Purdue University, West Lafayette, Indiana, vol. 61, No. 5, May 1984, pp. 928-931.

List et al., "*Oxidative Stability of Seed Oils Extracted with Supercritical Carbon Dioxide*," Journal of the American Oil Chemists' Society, vol. 66, No. 1, Jan. 1, 1989, pp. 98-101.

Gomez et al., "*Recovery of Grape Seed Oil by Liquid and Supercritical Carbon Dioxide Extraction: A Comparison with Conventional Solvent Extraction*," Chemical Engineering Journal and the Biochemical Engineering Journal, vol. 61, No. 3, Mar. 1996, pp. 227-231.

Dunford et al., "*Nutritional Components of Supercritical Carbon Dioxide Extracted Wheat Germ Oil*," 6th Symposium on Supercritical Fluids, Retrieved from the Internet: http://www.ensic.inpl-nancy.fr/ISASF/Docs/Versailles/Papers/PN37.pdf, 6 pages, Jan. 2003.

The EFSA Journal (2005) 278, "*Opinion of Scientific Panel on Dietetic Products, Nutrition and Allergies on a Request from the Commission Related to the Safety of Chia (Salvia Hispanica L.) Seed and Ground Whole Chia Seed as a Novel Food Ingredient Intended for Use in Bread*," http://www.efsa.eu.int/science/nda/nda_opinions/catindex_en.html, Oct. 5, 2005, pp. 1-12.

Laurange, "*Agua Fresca De Chia*" (Online) Aug. 30, 2007, XP002515363, Retrieved form the Internet: URL: http://www.saveursmexicaines.com/templates/home.php?page=86&content=128&;Ing=fr, 2 pages.

"*Supercritical Chia Seed Oil Could Become Leading Source of Omega-3 Linolenic Acid*" (Online) Nov. 30, 2005, XP002515364, Retrieved from the Internet: http://www.scientistilive.com/European-Food- Scientist/ingredients/Supercritical_Chia_Seed_Oil_could_become_leading_source_of_omega-3_linolenic_acid/14463, 4 pages.

"*Chia Samen CO2-to Extrakt*" (Online) Jul. 7, 2005, Rehlingen, De, Retrieved from the Internet: URL:http://www.flavex.com/hmd.html, 1 page.

"Deep extract supercritical CO2 extraction", May 2009, pp. 1-3.

"Stabilization-O2B peroxidation blocker system", Sep. 2011, pp. 1-3.

"Defatting technology", Sep. 2011, pp. 1-2.

"Extraction technology—the case for supercritical CO2", Sep. 2011, pp. 1-4.

"Perilla seed oil—supercritical CO2 extract", May 2012, pp. 1-4.

Kim et al., "Supercritical carbon dioxide extraction of perilla seed oil", Foods and Biotechnology, Korean Society of Food Science and Technology, vol. 5, No. 4, Jan. 1996, pp. 300-304.

\* cited by examiner

PLANT DERIVED SEED EXTRACT RICH IN ESSENTIAL FATTY ACIDS DERIVED FROM PERILLA SEED: COMPOSITION OF MATTER, MANUFACTURING PROCESS AND USE

RELATED APPLICATION(S)

This is a continuation-in-part application of application Ser. No. 12/419,321 filed Apr. 7, 2009 now U.S. Pat. No. 8,586,104, which is based upon provisional application Ser. No. 61/043,773 filed Apr. 10, 2008, the disclosures which are hereby incorporated by reference in their entirety.

FIELD OF THE INVENTION

This invention relates to plant-derived seed extracts and methods of making same.

BACKGROUND OF THE INVENTION

It is well known in the literature that Polyunsaturated Fatty Acids (PUFAs) of all types are highly susceptible to peroxide, free radical and light induced degradation including rancification and polymerization making them unsuitable for human consumption. For example, it is well known that flax seed oil, also known as linseed oil, readily undergoes free radical oxidation to advantageously form polymeric surfaces including oil based paints, hard furniture finishes and linoleum flooring. In addition, many companies offer flax seed oil for human consumption as a dietary supplement or food ingredient because of the high levels of PUFAs found in raw flax seed and its expeller pressed oils and more particularly Alpha-Linolenic Acid (ALA) and Linolenic Acid (LA). Many flax seed oil product labels suggest that the product must be refrigerated at all times due to the instability of such PUFAs in flax seed oil. Careful examination of the majority of commercially available flax seed oils obtained by expeller pressing, including those typically stored under refrigerated conditions, unfortunately reveals that they are unfit for human use based on their measured Peroxide Values (PVs). Such PV values above 3 meq/Kg (milliequivalents/gram) are deemed not suitable for salad oil applications and PV values above 10 meq/Kg are deemed to be unsuitable for human use because the measured PV value may be an early indicator of rancidity and free radical induced degradation. On the other hand, PV values taken alone do not adequately characterize such oils since a low PV value can also be associated with PUFA's that have already gone through the rancification process. Typical testing has revealed flax seed oil products sold for human consumption with observed PV's as high as 130 meq/kg also characterized with the odor associated with short chain aldehydes that make such oils "rancid" to olefactory senses.

Most raw seed based oils in common cooking and baking use, such as soybean, corn and canola seed oils naturally contain enough PUFAs making them unsuitable, without further processing, for use as cooking oils. Therefore unless such PUFA containing raw seed oils are hydrogenated to fully saturated triglycerides using hydrogen and a catalyst prior to their use in cooking applications, they are considered to be unfit for use as cooking oils. These oils are typically first isolated by, for example, expeller pressing the appropriate seed. The crude seed oil is then filtered to remove biomass. The resulting oil, containing significant levels of PUFAs, is then catalytically hydrogenated to reduce the PUFA content to levels suitable for use of the resulting oil in cooking applications. If the hydrogenation process is incomplete, however, the resulting mixtures are found to contain both undesirable heat labile PUFAs that quickly undergo rancification to small chain aldehydes in the resulting heated cooking oil as well as unsaturated trans-fatty acids which are believed to be detrimental to animal and especially human health.

Therefore, those skilled in the art will recognize the great difficulty in producing a shelf stable PUFA mixture wherein the PUFA content is as high as 70% wt/wt of the resulting seed extract from a natural seed source that then exhibits extraordinary room temperature stability.

Commonly assigned and copending patent application Ser. No. 12/419,321 discloses a *Salvia hispanica* L. derived seed oil extract composition of matter containing from 60-88% PUFAs in a ratio of from 3.1:1-3.3:1 of ALA to LA, 4-10% of C-18 mono-unsaturated fatty acid, 1-5% of C-18 saturated fatty acid and 4-8% of C-16 saturated fatty acid in a mixed triglyceride form stable at room temperature of 12-24 months containing a mixture of selected antioxidants. This chia derived composition has a very favorable ratio of ALA to LA (omega 3 to omega 6) of about 3.3:1 in one example. It is desirable to provide a composition of matter as a seed oil extract derived from other than chia and a method of manufacturing the seed oil that has equivalent or better PUFA content and ratios of ALA to LA and is shelf stable and exhibits room temperature stability.

SUMMARY OF THE INVENTION

A *perilla* seed oil extract provides a healthy source of omega-3 and contains a very favourable ratio of ALA to LA (omega-3 to omega-6) of about 6:1 in one example. The *perilla* oil is obtained by pressing the *perilla* seeds to initiate seed cracking, processing the cracked biomass using supercritical $CO^2$ fluid extraction, and collecting the extract to deliver more of the higher molecular weight compounds.

A composition of matter comprises a shelf stable, supercritical, $CO^2$ fluid extracted seed oil derived from a cracked biomass of *perilla frutescens*, the seed oil comprising from about 60 to about 95 percent w/w of PUFAs in a ratio of from about 4:1 to about 6:1 alpha-linolenic acid (ALA) to linoleic acid (LA) and a mixture of selected antioxidants.

In one example the selected antioxidants comprise a synergistic mixture of selected lipophilic and hydrophilic antioxidants. In another example the composition comprises lipophilic antioxidants either alone or in combination with at least one of: a) phenolic antioxidants including at least one of sage, oregano, and rosemary; b) tocopherol, c) tocotrienol(s), d) carotenoids including at least one of astaxanthin, lutein, and zeaxanthin; e) ascorbylacetate; f) ascorbylpalmitate g) Butylated hydroxytoluene (BHT); h) Docosapentaenoic Acid (BHA) and i) Tertiary Butyl hydroquinone (TBHQ). In another example a hydrophilic antioxidant or sequesterant is added comprising hydrophilic phenolic antioxidants including at least one of grape seed extract, tea extracts, ascorbic acid, citric acid, tartaric acid, and malic acid.

In another example the peroxide value of the seed oil is under 10.0 meq/Km. The composition can have supplemented to it docosahexaenoic acid (DHA) and/or eicosapentaenoic acid (EPA) in pectin or gelatin based confectionary dietary supplement delivery systems. The composition may include EPA, DHA, docosapentaenoic acid (DPA) or gamma-linlolenic acid (GLA), fish oil, krill oil, krill oil concentrate, borage oil, evening primrose oil, olive oil or other plant, animal or algal based seed or fruit oils admixed therein.

The composition of matter in yet another example comprises from about 85 to about 95 percent w/w of PUFAs. In another example, the composition has at least greater than 50 percent alpha-linolenic acid (ALA). The seed oil is shelf stable at room temperature up to 32 months. In another example the seed oil is derived from a premilled or flake-rolled cracked biomass of *perilla frutescens*.

A method is also disclosed of mitigating or preventing cardiovascular disease, arthritic pain and inflammation, platelet aggregation, or treating dry eye syndrome, premenstrual symptoms or modifying immune response in humans or animals by applying an effective amount of a dietary supplement, food or beverage that has added thereto a composition mixed therewith and comprising a supercritical, $CO^2$ fluid extracted seed oil derived from a cracked biomass of *perilla frutescens*, the seed oil comprising from about 60 to about 95 percent w/w of PUFAs in a ratio of from about 4:1 to about 6:1 alpha-linolenic acid (ALA) to linoleic acid (LA) and a mixture of selected antioxidants.

In one example, an emulsifying agent is added. Nano- and/or micro-particles of rice or sugarcane based policosanol can be added for providing a heart healthy dietary supplement. Also, a stabilized oil can be dispersed in a fruit juice concentrate, fruit puree or other water based flavoring in the presence of maltodextrin, or other carbohydrates, and an emulsifying or emulsion stabilization agent that is vacuum spray dried to form an amorphous or crystalline solid suitable for use as a flavoring ingredient carrying stabilized PUFAs in flavored dietary supplements, foods and beverages.

Oil based flavors and fragrances suitable for use as an ingredient in foods, beverages and cosmetics can be added. Docosahexaenoic acid (DNA) and/or eicosapentaenoic acid (EPA) can be added to supplement, including adding EPA, DHA, docosapentaenoic acid (DPA) or gamma-linlolenic acid (GLA), fish oil, krill oil, krill oil concentrate, borage oil, evening primrose oil, olive oil or other plant, animal or algal based seed or fruit oils.

A method of manufacturing a *perilla frutescens* derived seed oil comprising from about 60 to about 95 percent w/w of PUFAs in a ratio of from about 4:1 to about 6:1 alpha-linolenic acid (ALA) to linoleic acid (LA) is disclosed and comprises processing *perilla frutescens* seed preferably in the absence of oxygen to obtain a biomass having a desired particle size distribution, subjecting the resulting biomass to supercritical fluid $CO^2$ extraction, collecting a resulting seed oil fraction, and separating water in the fraction.

The method also comprises in one example treating any resulting seed oil fraction with antioxidants to impart a desired room temperature stability. The method further comprises controlling the extent of oil extraction by particle size distribution. The method further comprises adding propane in admixture with supercritical $CO^2$ in the supercritical state as an extraction solvent. In one example, the method further comprises extracting solvent using hexane extraction at or near atmospheric pressures and the resulting boiling point of hexane in the absence of oxygen, separating the resulting water from the oil/hexane mixture and removing the hexane solvent by distillation at or below atmospheric pressure in the absence of oxygen.

The method further comprises adding lipophilic antioxidants to increase the room temperature stability of the resulting oil. The method further comprises adding lipophilic antioxidants either alone or in combination with at least one of a) phenolic antioxidants including at least one of sage, oregano, and rosemary; b) tocopherol, c) tocotrienol(s), d) carotenoids including at least one of astaxanthin, lutein, and zeaxanthin; e) ascorbylacetate; f) ascorbylpalmitate g) Butylated hydroxytoluene (BHT); h) Docosapentaenoic Acid (BHA) and i) Tertiary Butyl hydroquinone (TBHQ). The method further comprises treating any resulting dewatered seed oil with bleaching clay or activated carbon.

The method further comprises adding a hydrophilic antioxidant or sequesterant comprising hydrophilic phenolic antioxidants including at least one of grape seed extract, tea extracts, ascorbic acid, citric acid, tartaric acid, and malic acid. The method further comprises premilling or roller press flaking the *perilla frutescens* seed to obtain the desired particle size. The method further comprises treating the premilled or roller press flaked seed with a lipophilic or hydrophilic antioxidant prior to solvent extraction. The method further comprises processing the *perilla frutescens* seed with or without the addition of hydrophilic or lipophilic antioxidants during the particle sizing process. The *perilla frutescens* derived seed oil is stable at room temperature for about 12 to about 32 months. The method further comprises performing supercritical extraction in the presence of lipophilic and or hydrophilic antioxidants.

BRIEF DESCRIPTION OF THE DRAWINGS

Other objects, features and advantages of the present invention will become apparent from the detailed description of the invention which follows, when considered in light of the accompanying drawings in which.

DETAILED DESCRIPTION OF THE PREFERRED EMBODIMENTS

Figure 1:
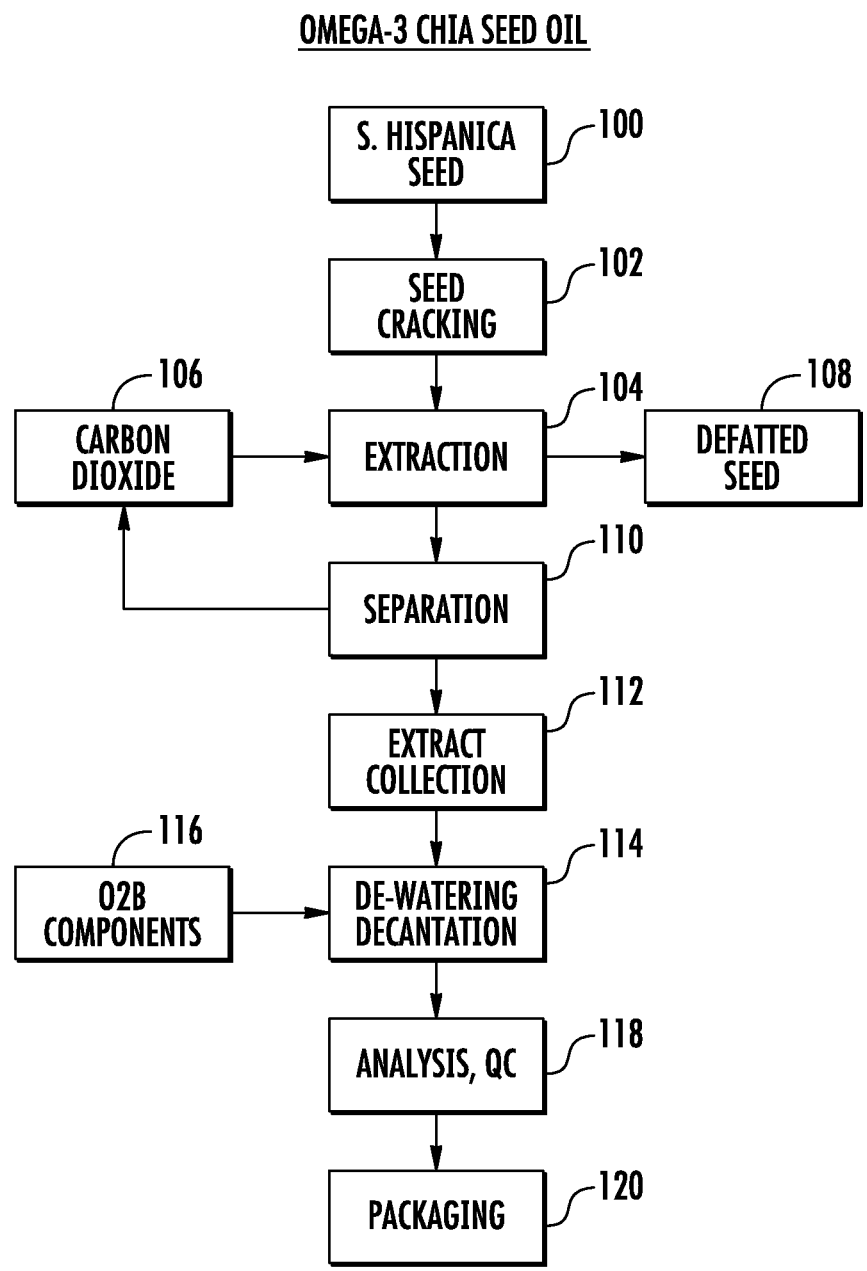
FIG. 1 is a flowchart illustrating a production diagram as a flowchart for producing omega-3 chia seed oil such as sold under the tradename Chia Gold™ by Valensa International of Eustis, Fla.

The present invention will now be described more fully hereinafter. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Commonly assigned and copending parent application Ser. No. 12/419,321 discloses a room temperature, shelf stable mixture of an approximate 3.1:1 to about 3.3:1 mixture of alpha-linolenic acid ("ALA", "Omega-3 polyunsaturated fatty acid" ("PUFA")) to linoleic acid ("LA", "Omega-6 PUFA) that has been prepared in the presence of limited amounts of saturated and mono-unsaturated fatty acids as their mixed triglycerides by the use of either supercritical fluid $CO^2$ solvent extraction of premilled *Salvia hispanica* L. seed alone, and more particularly, supercritical fluid $CO^2$ solvent extraction in the presence of mixtures of hydrophilic and lipophilic antioxidants, or, by the use of a common organic solvent extraction such as hexane or by the use of expeller pressing techniques. The supercritical $CO^2$ extraction is preferred.

Such Omega-3 and Omega-6 PUFAs are well known as essential fatty acids in man and many animals, which are useful in humans and animals in promoting, for example, a heart healthy condition in man. It is also well known, however, that PUFAs are extremely susceptible to rapid, uncontrollable free radical mediated degradation.

The composition of matter disclosed in the copending '321 application includes a supercritical $CO^2$ *Salvia hispanica* L. derived seed oil comprising from 60-88% PUFAs in a ratio of from about 3.1:1-3.3:1 of alpha-linolenic acid (ALA) to linoleic acid (LA), 4-10% of C-18 mono-unsaturated fatty acid, 1-5% of C-18 saturated fatty acid and 4-8% of C-16 saturated fatty acid in a mixed triglyceride form that is stable at room temperature for 12-24 months and comprising a mixture of selected antioxidants.

The composition of matter includes dietary supplement ingredients such as docosahexaenoic acid (DHA) and/or eicosapentaenoic acid (EPA) in pectin or gelatin based confectionary dietary supplement delivery systems. EPA, DHA, docosahexaenoic acid (DPA) or gamma-linlolenic acid (GLA), fish oil, krill oil, krill oil concentrate, borage oil, evening primrose oil, olive oil or other plant, animal or algal based seed or fruit oils are admixed therein either alone or in combination. Lipophilic antioxidants are added either alone or in combination with at least one of a) phenolic antioxidants including at least one of sage, oregano, and rosemary; b) tocopherol, c) tocotrienol(s), d) carotenoids including at least one of astaxanthin, lutein, and zeaxanthin; e) ascorbylacetate; f) ascorbylpalmitate g) Butylated hydroxytoluene (BHT); h) Docosapentaenoic Acid (BHA) and i) Tertiary Butyl hydroquinone (TBHQ). As disclosed, a hydrophilic antioxidant or sequesterant includes hydrophilic phenolic antioxidants including at least one of grape seed extract, tea extracts, ascorbic acid, citric acid, tartaric acid, and malic acid.

A method of manufacturing and method of using the composition is also set forth in the '321 application.

As further disclosed in this incorporated by reference '321 application, this PUFA rich seed oil extract is prepared from *Salvia hispanica* L. seed which contains one of nature's more favorable seed based concentrations and ratios for the essential fatty acids, and more specifically, the essential fatty acids ALA and LA in a ratio of approximately 3.3:1 as a mixture of ALA and LA that is stable at room temperature for long periods of time when desirably and appropriately treated with antioxidants either before, during, or after (or any combination thereof). A shelf life of 12-24 months has been found.

Such oils are used either alone or advantageously in combination with other ingredients, for example, algae, plant or fish derived alpha-linolenic acid (ALA) or linoleic acid (LA) metabolites such as eicosapentaenoic acid (EPA), docosapentaenoic acid (DPA), gamma-linlolenic acid (GLA) or docosahexaenoic acid (DHA) or any combination thereof, incorporated into appropriate foods, beverages or dietary supplements for the prevention or mitigation of such diseases as cardiovascular disease, arthritis, pain, blood clotting, dry eyes and brain health.

Such disease mitigation has been associated with the competitive control of the LA metabolic cascade and the resulting metabolic cascade products from LA metabolism known commonly as eicosanoids, such as the series 2 and 3 prostaglandins and thromboxanes, the series 4 leucotrienes and lipoxins and the series 5 leuotrienes all of which are potent platelet aggregators and/or inhibitors, pro-inflammatories, vasodilators, bronchoconstrictors, or anti-asthmatics and the like.

The consumption of ALA has been shown to be a very effective competitive substrate of delta-6 desaturase, which is known to be the rate limiting enzymatic step in both ALA and LA metabolism to the metabolic products discussed above.

Attempted extraction of *Saliva hispanica* L. unmilled seed, using supercritical $CO^2$ even at extraordinarily high pressures of 1000 bar or hexane solvent at atmospheric pressures, yields very little, if any, seed oil, therefore the seed must be milled prior to extraction. The extent of the milling, as measured by particle size distribution, is advantageous to the extraction process in accordance with a non-limiting aspect since the higher the surface area, the higher will be the efficiency and completeness of the extraction process by either organic solvent based or supercritical fluid based processes. In addition, it is often advantageous to mill the seed in a blanket of inert gas such as nitrogen to prevent per-oxidative processes from taking place that would otherwise be initiated in the presence of air or oxygen and light.

In one embodiment, *Salvia Hispanica* L. whole seed is either first commutated in a standard knife or hammer mill or more preferably roller milled, preferably under a cold nitrogen atmosphere, to produce a cracked seed biomass. The seed biomass is preferably treated with one or more hydrophilic and/or lipophilic antioxidants by mixing the antioxidants to the resulting biomass. In another embodiment, the antioxidant may be advantageously added to the seed prior to or during the milling process or at the point of extraction without pre-blending the antioxidants evenly throughout the resulting biomass due to the nature of the extraction process. The biomass is then transferred to a supercritical fluid extraction unit for separation of the seed oil from the cracked or flake-rolled biomass.

Alternatively, the pre-prepared biomass can be transferred to a common hexane solvent extractor, or an expeller press for example, and the oil extracted from the biomass accordingly. Preferably either process is conducted in the absence of oxygen or air.

The supercritical fluid extraction of the milled seed admixed with hydrophilic and/or lipophilic antioxidants is accomplished by subjecting the premilled cracked or flake-rolled seed to supercritical $CO^2$, or $CO^2$ and propane as a co-solvent, or supercritical propane alone at from 40-1000 bar at from 30-100 Deg. C. More preferably the seed oil is extracted from the biomass between 50-800 bar at 50-90 deg. C. in such $CO^2$ amounts measured in kgs/kg of biomass and for such times as may be required to extract large portions of the seed oil content from the biomass. In addition, entrainment solvents can be added to the supercritical fluid to further enhance the efficacy of such extractions. For example, supercritical carbon dioxide extraction of the biomass can be enhanced by the addition of propane to the supercritical extraction fluid.

The resulting seed oil dissolved in supercritical solvent(s) is next allowed to fractionate in two separate pressure step-down stages allowing the collection of a light and heavy fraction of seed oil extract. This light fraction also contains water that has been co-extracted from the seed mass. The resulting seed oil, after degassing, is separated from any water that may have been carried over during the extraction of the biomass containing the water. The light fraction of the seed oil extract is rich in taste and odor components and may be admixed with the heavy fraction or may be discarded depending on the desired product characteristics.

After separation of the water remaining in each fraction, the fractions are then held under nitrogen or other inert gas and additional amounts of lipophilic and/or hydrophilic antioxidants may then be added. In addition, the resulting fractions may also be treated with bleaching clay, carbon and such other processing aids as may be required to render the oil suitable for its intended use in humans and animals.

The PV of the resulting seed oil extract is typically under 2.0 meq/Km, while accelerated decomposition, using a Rancimat instrument, remarkably indicates an extrapolated room temperature shelf life of from about 1-2 years. When the same process is repeated without the use of antioxidants, the resulting PV is surprisingly under 10.0 meq/Kg most probably due to the use of supercritical $CO^2$ resulting in minimal exposure of the oil to oxygen species. However, the resulting oil quickly begins to build peroxide value in the presence of air even when stored at temperatures of 0 Degs. C. In addition, such unstabilized oils, under accelerated rancimat testing exhibit very poor stability to heat and oxygen unlike the rancimat performance observed in stablizied oils derived from the process described above.

The resulting supercritical fluid seed oil extract of the invention contains from 60-88% PUFAs in a ratio of from 3.1:1-3.3:1 of ALA:LA, 4-10% of C18 mono-unsaturated fatty acid, 1-5% of C-18 saturated fatty acid and 4-8% C-16 saturated fatty acid composition in a mixed triglyceride form depending on the seed source employed.

On the other hand, if the process described above is conducted without the use of hydrophilic and/or lipophilic antioxidants, the resulting seed oil extract exhibits an initial low PV but accelerated stability testing using a Rancimat instrument indicates an extrapolated room temperature shelf stability of less than two months.

The stability of the resulting oil at room temperature that is manufactured without the use of added antioxidants cannot be easily explained because of the available levels of the powerful natural antioxidants found in *Salvia hispanica* L. whole seed whose activity can be easily measured in Oxygen Radical Absorbance Capacity (ORAC) units. *Salvia hispanica* L. has a measured ORAC number of 3000 micromoles TE ORAC units/gram of seed and is known to contain such antioxidants as myricetin, quercetin, kaempferol, caffeic acid, and chlorogenic acid. In addition, it is well known that the *Salvia hispanica* L. whole seed, unlike many other seeds bearing PUFA containing oil, exhibits a shelf life of at least 5 years due to its structure and the naturally occurring antioxidants available in the seed matrix.

In addition, cold pressing of *Salvia hispanica* L. whole seed also produces unstable seed oil without careful addition of appropriate antioxidants to the seed prior to the expeller pressing process.

In a non-limiting example the composition of matter is formed from a supercritical $CO^2$ derived *Salvia hispanica* L. derived seed oil comprising from 60-88% PUFAs in a ratio of from 3.1:1-3.3:1 of alpha-linolenic acid (ALA) to linoleic acid (LA), 4-10% of C-18 mono-unsaturated fatty acid, 1-5% of C-18 saturated fatty acid and 4-8% of C-16 saturated fatty acid in a mixed triglyceride form that is stable at room temperature for 12-24 months and comprising a mixture of selected antioxidants.

It includes docosahexaenoic acid (DHA) and/or eicosapentaenoic acid (EPA) in pectin or gelatin based confectionary dietary supplement delivery systems and in another aspect EPA, DHA, docosapentaenoic acid (DPA) or gamma-linlolenic acid (GLA), fish oil, krill oil, krill oil concentrate, borage oil, evening primrose oil, olive oil or other plant, animal or algal based seed or fruit oils are admixed therein.

Lipophilic antioxidants are added either alone or in combination with at least one of a) phenolic antioxidants including at least one of sage, oregano, and rosemary; b) tocopherol, c) tocotrienol(s), d) carotenoids including at least one of astaxanthin, lutein, and zeaxanthin; e) ascorbylacetate; f) ascorbylpalmitate g) Butylated hydroxytoluene (BHT); h) Docosapentaenoic Acid (BHA) and i) Tertiary Butyl hydroquinone (TBHQ). The hydrophilic antioxidant or sequesterant includes hydrophilic phenolic antioxidants including at least one of grape seed extract, tea extracts, ascorbic acid, citric acid, tartaric acid, and malic acid in another aspect.

A method of manufacturing a *Salvia hispanica* L. derived seed oil in another non-limiting example is set forth. The seed oil comprises from 60-88% PUFAs in a ratio of from 3.1:1-3.3:1 of alpha-linolenic acid (ALA) to linoleic acid (LA), 4-10% of C-18 mono-unsaturated fatty acid, 1-5% of C-18 saturated fatty acid and 4-8% of C-16 saturated fatty acid in a mixed triglyceride form that is stable at room temperature for 12-24 months and includes antioxidants. The method includes milling or roller press flaking *Salvia hispanica* L. seed in the absence of oxygen to obtain a desired particle size distribution with or without the addition of hydrophilic or lipophilic antioxidants during the particle sizing process. The resulting biomass is subjected to supercritical fluid $CO^2$ extraction in the presence of lipophilic and/or hydrophilic antioxidants. Any resulting seed oil fractions are collected. The water is separated in each fraction.

Any resulting seed oil fractions can be treated with additional antioxidants to afford a desired room temperature stability. The extent of oil extraction can be controlled by particle size distribution of the milled or flaked seed. Propane can be added in mixture with supercritical $CO^2$ in the supercritical state as an extraction solvent. In yet another aspect solvent can be extracted using hexane extraction at or near atmospheric pressures and the resulting boiling point of hexane in the absence of oxygen, separating the resulting water from the oil/hexane mixture and removing the hexane solvent by distillation at or below atmospheric pressure in the absence of oxygen.

Lipophilic antioxidants can be added to increase the room temperature stability of the resulting oil. The lipophilic antioxidants can be added either alone or in combination with at least one of a) phenolic antioxidants including at least one of sage, oregano, and rosemary; b) tocopherol, c) tocotrienol(s), d) carotenoids including at least one of astaxanthin, lutein, and zeaxanthin; e) ascorbylacetate; f) ascorbylpalmitate g) Butylated hydroxytoluene (BHT); h) Docosapentaenoic Acid (BHA) and i) Tertiary Butyl hydroquinone (TBHQ). The resulting dewatered seed oil can be treated with bleaching clay or activated carbon.

Premilled or roller press flaked seed can be treated with a lipophilic or hydrophilic antioxidant(s) prior to solvent extraction. The hydrophilic antioxidant or sequesterant can be formed from hydrophilic phenolic antioxidants including at least one of grape seed extract, tea extracts, ascorbic acid, citric acid, tartaric acid, and malic acid.

A method of mitigating or preventing cardiovascular disease, arthritic pain and inflammation, platelet aggregation, or treating dry eye syndrome, premenstrual symptoms or modifying immune response in humans or animals is set forth by applying an effective amount of a dietary supplement, food or beverage to which has been a composition mixed therewith and comprising a *Salvia hispanica* L. derived seed oil comprising from 60-88% PUFAs in a ratio of from 3.1:1-3.3:1 of alpha-linolenic acid (ALA) to linoleic acid (LA), 4-10% of C-18 mono-unsaturated fatty acid, 1-5% of C-18 saturated fatty acid and 4-8% of C-16 saturated fatty acid in a mixed triglyceride form that is stable at room temperature for 12-24 months and includes antioxidants.

In one aspect, an emulsifying agent is added. In another aspect, nano- and/or micro-particles of rice or sugarcane based polycosanol are dispersed for enhancing a heart healthy dietary supplement. A stabilized oil in a fruit juice concentrate, fruit puree or other water based flavoring is dispersed in the presence of maltodextrin, or other carbohydrates, and a suitable emulsifying or emulsion stabilization agent that is vacuum spray dried to form an amorphous or crystalline solid suitable for use as a flavoring ingredient carrying stabilized PUFAs in flavored dietary supplements, foods and beverages. In yet another aspect, oil based flavors and fragrances suitable for use as an ingredient in foods, beverages and cosmetics are added. ALA and LA are also added as essential fatty acids.

It has also been found that the use of a *perilla* seed oil extract instead of the disclosed chia seed oil is advantageous and contains a very favorable ratio of ALA to LA (omega-3 to omega-6) of as high as about 6:1 in some examples as compared to chia seed oil that is typically about 3.3:1 ALA to LA. *Perilla* seed oil extract as obtained, in accordance with a no-limiting example, is thus an even healthier source of omega-3 than chia seed oil in various non-limiting examples.

FIG. 1 is a flowchart showing a production diagram for a sequence of steps for producing omega-3 chia seed oil such as sold under the tradename Chia Gold™ by Valensa International of Eustis, Fla. The salvia hispanica seed is provided (block 100) and seed cracking occurs (block 102) to form a cracked biomass. Various techniques for seed cracking and forming the biomass can be used as described above. The supercritical $CO^2$ extraction (block 104) uses ultra high pressure carbon dioxide extraction technology and supplied $CO^2$ (block 106) such as the DEEP EXTRACT® manufacturing process developed by Valensa International of Eustis, Fla. The defatted seed as a flour, for example, (block 108) is produced. Separation of the different portions occurs such as by fractionating the seed oil extract (block 110) as described above. The extract is collected (block 112). Dewatering and decantation occurs (block 114) and antioxidants are added (block 116) such as the OTB® Per Oxidation blocker system from Valensa International. Quality control analysis occurs (block 118) and the final oil packaged (block 120).

Figure 2:
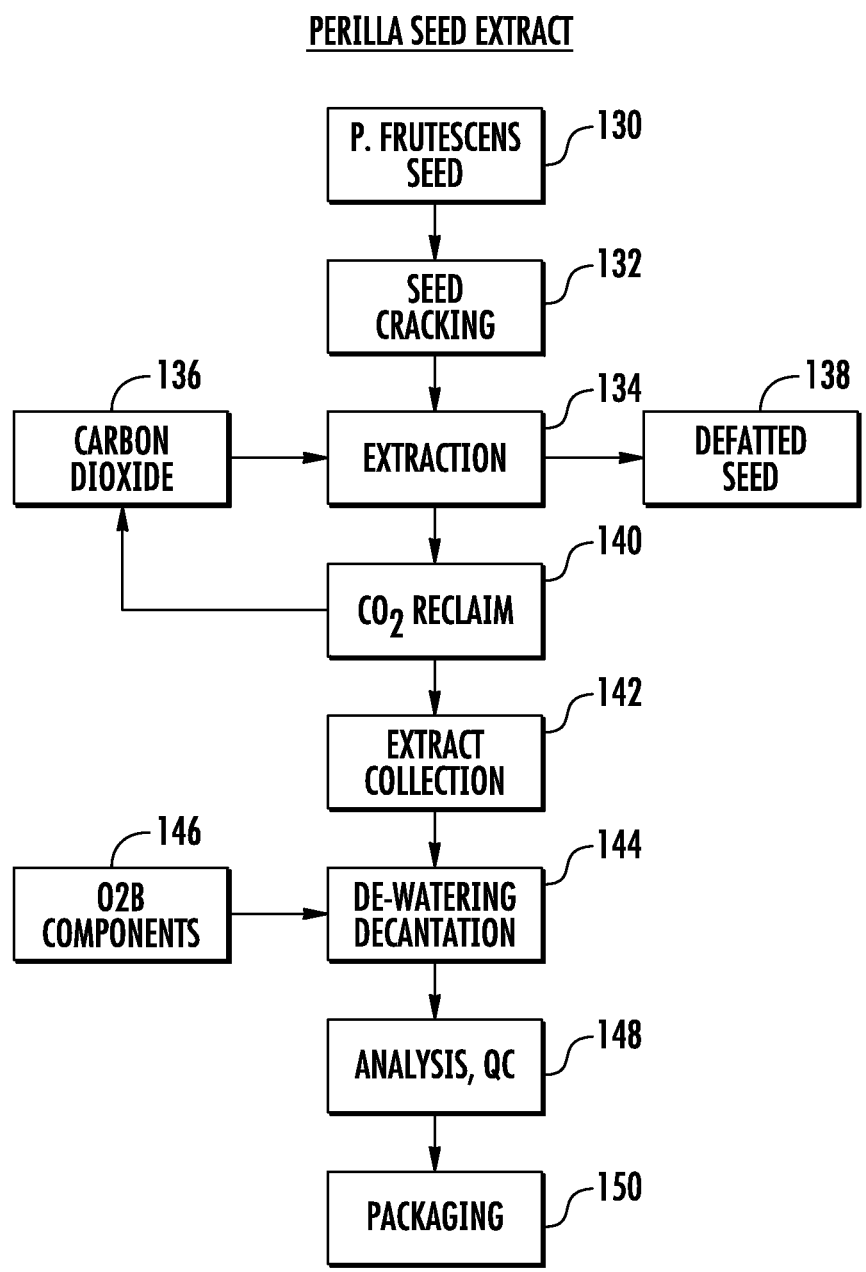
FIG. 2 is another production diagram as a flowchart showing basic steps for manufacturing a *perilla* seed extract in accordance with a non-limiting example.

FIG. 2 shows a second production diagram as a flowchart for producing the *perilla* seed oil extract in accordance with a non-limiting example. The process begins with a source of the *perilla* seed also known as *perilla frutescens* seed (block 130). Similar to the process with the omega-3 chia seed oil, seed cracking occurs (block 132) to form a cracked seed biomass followed by the extraction (block 134) using the supercritical $CO^2$ extraction and supplying carbon dioxide (block 136) to produce the defatted seed (block 138) that is partially or wholly defatted *perilla* seed as a cake residue with virtually no fat or oil. The other portion is the oil and the $CO^2$ is reclaimed (block 140). Similar to the omega-3 chia seed oil, the extract is collected (block 142) and dewatering and decantation occurs (block 144). Antioxidants such as the OTB® components as described before are added (block 146) and the quality control analysis occurs (block 148) followed by packaging (block 150).

The *perilla* seed extract can have a range of values for its fatty acid profile. Total fatty acids, peroxide values and other component values are described in Table 1 below showing an analysis of *perilla* seed extract and various parameters, specifications and results as a non-limiting example. Results can vary of course for different samples.

TABLE 1

Ingredients:
*Perilla* (*Perilla frutescens* (L.) Britton) Seed Oil, O2B ™
Botanical peroxidation blocker including refined nonGMO soybean
mixed tocopherols and spice extract.

| Parameter | Specification | Result |
|---|---|---|
| Description | Clear yellow oil, pourable at room temperature | Conforms |
| Odor | Mild | Conforms |
| Solubility | Insoluble in water, miscible with oils | Conforms |
| Fatty Acid Profile (%) | VQP-050 (GC) | |
| Palmitic Acid | | 6.3 |
| Stearic Acid | | 1.9 |

TABLE 1-continued

Ingredients:
*Perilla* (*Perilla frutescens* (L.) Britton) Seed Oil, O2B ™
Botanical peroxidation blocker including refined nonGMO soybean
mixed tocopherols and spice extract.

| Parameter | Specification | | Result |
|---|---|---|---|
| Oleic Acid | | | 22.3 |
| Linoleic Acid | | | 9.7 |
| α-Linolenic Acid | >56 | | 59.8 |
| Total Fatty Acids (% w/w) | 85 ... 95 | | 88.6 |
| Peroxide Value (meqO$_2$/kg) | <10 | VQP-049 | 2.3 |
| Water Content (%) | <1.5 | VQP-048 | <0.2 |
| Heavy Metals (ppm) | <10 | ICP-MS | <1 |
| Microbiological Data (cfu/g) | | | |
| Total Aerobic Microbial Count | <10$^3$ | USP <61> | <100 |
| Combined Yeast & Mold | <10$^2$ | USP <61> | <100 |
| *E. coli*/Total Coliforms | <10 | AOAC 991.14 | <10 |

(all values as is basis)
All of the ingredients are GMO free. Therefore this product is in accordance with EU regulations 1830/2003 and 1829/2003. The Product has not been treated with gamma rays.

Table 2 show accelerated stability testing of the *perilla* seed extract with an OTB® per oxidation blocker and Table 3 shows the accelerated stability testing of a *perilla* seed extract sample produced by Valensa International of Eustis, Fla. as compared to chia seed extracts such as the Chia Gold™ which is produced by the process shown in FIG. 1.

TABLE 2

Accelerated Stability Testing of Valensa *Perilla* Seed
Extract with O2B ®

| | Rancidity Induction Time (hr)$^1$ | Shelf Life @20° C. (yr)$^2$ |
|---|---|---|
| *Perilla* Oil (without O2B) | 7 | 0.5 |
| *Perilla* Oil (with O2B) | 42 | 2.8 |

$^1$Rancimat induction time measured in hours with air bubbling through heated oil (90° C.) in the light.
$^2$Rancimat data is a function of accelerated high heat and oxygen exposure. Extrapolated data plots are assumed linear in the presence of air and light at 20° C. however, if product is stored at 20° C. in an air and light barrier package, then shelf stability is at least doubled.

TABLE 3

Accelerated Stability Testing of Valensa *Perilla* Seed
and Chia Seed Extracts with O2B ®

| | Rancidity Induction Time (hr)$^1$ | Shelf Life @20° C. (yr)$^2$ | Shelf Life Increase (%) |
|---|---|---|---|
| *Perilla* Oil (without O2B) | 7 | 0.5 | 611% |
| *Perilla* Oil (with O2B) | 42 | 2.8 | |
| Tresalbio Chia Oil (without O2B) | 12 | 0.4 | 603% |
| Tresalbio Chia Oil (with O2B) | 73 | 2.2 | |
| ChiaGold Oil (without O2B) | 9 | 0.3 | 663% |
| ChiaGold Oil (with O2B) | 60 | 1.8 | |

$^1$Rancimat induction time measured in hours with air bubbling through heated oil (80-90° C.) in the light.
$^2$Rancimat data is a function of accelerated high heat and oxygen exposure. Extrapolated data plots are assumed linear in the presence of air and light at 20° C. however, if product is stored at 20° C. in an air and light barrier package, then shelf stability is at least doubled.

Table 1 illustrates various values and shows the total fatty acids (% w/w) is 85 to about 95 and has in that particular example a result of 88.6. It should be understood that the seed oil could possibly have as low as about 60% w/w of PUFAs and as high as about 95% and a ratio of from about 4:1 to about 6:1 ALA to LA. The peroxide value of the seed oil is typically under 10.0 meq/Km. The PUFAs typically comprise at least greater than 50% ALA and in the example shown in Table 1 is greater than 56% and in one particular example shown in FIG. 1 is 59.8. The seed oil is shelf stable at room temperature up to 32 months in a particular example. Other data is shown such as specific components of the fatty acids and the water content, heavy metals in PPM, and microbiological data in CFU/G, such as the total aerobic microbial count, a combined yeast and mold and E. coli/total coliforms. All the values are an as-is basis and the ingredients are GMO free. Therefore, this product is in accordance with EU regulations 1830/2003 and 1829/2003. This product had not been treated with gamma rays. Ingredients include the perilla (perilla frutescens (L) Britton) seed oil, OTB® botanical per oxidation blocker including refined non-GMO soybean mixed tocopherols and spice extracts. GMO corresponds to genetically modified organisms, and thus, non-GMO refers to non-genetically modified organisms. The soybean had not been created through gene-splicing techniques of biotechnology or genetic engineering.

The production diagram in FIG. 2 shows the process used to obtain the perilla seed extract in accordance with a non-limiting example. The extraction technology has been described relative to the chic seed oil and extract in the incorporated by reference parent application and described above in some detail. It should be understood that extraction technology creates materials for human nutrition and supplementation and offers various benefits including enhanced efficacy with the isolation of key components to allow higher dosage and targeted performance. Extraction allows standardization. Natural materials tend to vary in make-up and extraction makes them consistent. It is also convenient because smaller dosages of high efficiency materials allow a consumer to more easily obtain the required levels of nutrients in a daily regimen. There is also enhanced safety because extraction gives more of the desired products and less of what is not desired. Extraction allows the removal of compounds that are not optimal for human health from natural materials.

The desired extraction technology uses the DEEP EXTRACT® process from Valensa International as an ultra high pressure carbon dioxide extraction technology that yields micronutrients and has high extraction efficiency to deliver more of the higher molecular weight compounds that more closely track the natural source materials. The process is flexible and allows for possible fractionation of the product if desired and delivery of specific compounds out of the raw material.

This extraction process, such as the DEEP EXTRACT® process, offers a more gentle treatment of high value raw materials at temperature levels that are substantially below those used in other expeller press processes and some chemical solvent extraction processes in the absence of oxygen. This reduces the degradation of liable compounds, chemical change of a component and the oxidation potential. The supercritical $CO^2$ process offers virtual sterilization of the finished product and biomass, which are untouched by chemical solvents and stay "natural" as before extraction. Selective fractionation in some example is advantageous. Pressure is a main tool used to tailor the resulting fractionated products for product quality and efficient manufacturing. Because the $CO^2$ extraction is an all-natural and organic process, the final product is devoid of impurities and residues and delivers through the supercritical $CO^2$ extraction the high molecular weight compounds such as sterols, carotenoids and long chain alcohols.

Supercritical $CO^2$ extraction is advantageous over other methods used for extracting botanicals, including tinctures (usually alcohol extraction; steam distillation; expeller pressing, sometimes referred to as "cold pressing," and chemical solvent extraction). Chemical solvent extraction technology using strong solvents and supercritical $CO^2$ technology using high pressures typically offer the most comprehension extraction of a botanical. Supercritical $CO^2$ extraction conducted under very high pressure is advantageous. When carbon dioxide gas ($CO^2$) is compressed above 73 bar at a temperature above 31 degrees C. (87.8 degrees Fahrenheit), it transforms into a dense gas as supercritical $CO^2$, which has an extremely high solvating capacity and a power to extract constituents of botanicals. Its solvating capacity is a function of its density and by changing its density with pressure, the manufacturer is able to select the quality, quantity and specific principles of the targeted extract. Supercritical $CO^2$ is biologically compatible and generally regarded as safe (GRAS) by the FDA. It is also non-flammable and environmentally sound.

Any defatted cake resulting from the supercritical $CO^2$ process is typically viable and can be marketed or used for further processing in a wide range of human/food applications. Sometimes the defatted cake is the primary product and the oil is secondary as described in commonly assigned U.S. patent application Ser. No. 12/349,100 as filed on Jan. 6, 2009 and published as U.S. Patent Publication No. 2009/0181127, the disclosure which is hereby incorporated by reference in its entirety. That application describes a chia seed composition as a composition of matter formed from a stable, defatted whole grain flour derived from salvia hispanica L. whole ground seed using a suitable solvent such as using supercritical $CO^2$ fluid extraction. This chia seed extraction demonstrates that after processing of supercritical $CO^2$, the extract cake contains in some examples virtually no fat or oil and the resultant powder is approximately 50% protein and 50% carbohydrates that exist essentially as fiber.

The supercritical $CO^2$ process offers a gentle treatment of high value raw materials at temperature levels substantially below those used in expeller press in some chemical solvent extraction operations in the absence of oxygen. This reduces the degradation of labile compounds, chemical changing components and the oxidation potential. The supercritical $CO^2$ process offers virtual sterilization of the finished product and biomass that are untouched by chemical solvents and stay "natural" as they were before extraction. It also allows the advantage of fractionating the extracted components selectively with pressure tailoring the resulting fractionated products for product quality and efficient manufacturing. This addresses pesticide/insecticide residues and handle concerns about microorganisms that are present in expeller press materials.

The extract as shown in FIG. 2 is dewatered and decantated and antioxidants added such as the Valensa OTB® per oxidation blocker system as a stabilizer to ensure that the botanical extract reaches a consumer in an efficacious and safe form. Stabilization with the OTB® components is a key to shelf life and continued product quality and is advantageous over using preservatives to stabilize natural materials, which is often seen as a negative by consumers. The OTB® per oxidation blocker system used by Valensa is 100% natural, non-GMO, and protects sensitive oils and particularly the highly unsaturated oils derived from fish and botanicals from the manufacture to consumption. The OTB® per oxidation blocker is a synergistic proprietary formulation of powerful natural compounds including astaxanthin, phenolic antioxidants and natural tocopherols. This technology prevents destructive oxidative, photochemical and rancification reactions. It protects expensive and sensitive compounds such as carotenoids and polyunsaturated fatty acids and can boost the effectiveness of other antioxidants such as vitamin E because it chemically quenches stable vitamin E free radicals. The antioxidants have in-vivo activity to protect both products and people.

*Perilla* has a number of essential oils. These are extracted from the leaves of *perilla*. About 50% to about 60% of perillaldehyde is responsible for so much of the aroma and taste of *perilla*. There are other terpenes such as limonene, caryophyllene and farnesene. There are other chemotypes such as *perilla* keytone (PK), esholzia keytone (EK), perillene (PL), and various phenylpropanoids such as myristicin, dillapiole and elemicin. Citral is a type rich in rosefuran. *Perilla* oil typically is obtained by pressing the seeds of *perilla* that contain about 35% to about 45% oil. In some parts of Asia, *perilla* oil is an edible oil valued for medicinal benefit. Typically, *perilla* oil is a rich source of omega-3 fatty acid alpha-linolenic acids. As a drying oil, it is similar to tung oil or linseed oil and is sometimes used in paint, varnish, linoleum, printing ink, lacquers and other protective waterproof coatings. In Japan, the oxime of perillaldehyde (perillartin) is used as an artificial sweetener and typically is about 2,000 times sweeter than sucrose.

Rancimat testing has shown the advantages of the *perilla* seed oil extract in accordance with a non-limiting example. This method is an accelerated oxidation test that is a simple, quick and efficient way to screen the effectiveness of the antioxidants used in liquid fats and oils. Typically, the rancimat test is an accelerated oxidation test in which the oil or fat to be tested is run at an elevated temperature exposing the sample to air accelerating the oxidation process of the oil. Auto oxidation typically occurs in a few hours instead of the months or years and the metabolites are driven off into a measuring vessel that measures the change in conductivity in one example. This would indicate the point at which the formation of volatile carboxylic acids and oxidation has occurred.

It is also possible to disperse nano- and/or micro-particles of rice or sugar cane based policosanol for providing a heart healthy dietary supplement. Such dietary supplement composition additives are disclosed in commonly assigned U.S. Pat. No. 7,959,950, the disclosure which is hereby incorporated by reference in its entirety. This human or animal dietary supplement composition includes one or more long chain (C24-C36) primary alcohols (policosanols) dispersed in food-grade oils or fats where the average policosanol particle size is greater than 2 microns and less than 10 microns in one example, and in another example, less than 100 microns.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that the modifications and embodiments are intended to be included within the scope of the dependent claims.

That which is claimed is:

1. A composition of matter comprising a shelf stable, supercritical, $CO^2$ fluid extracted seed oil derived from a cracked biomass of *perilla frutescens*, the seed oil comprising from 60 to 95 percent w/w of PUFAs in a ratio of from 4:1 to 6:1 alpha-linolenic acid (ALA) to linoleic acid (LA) and a mixture of selected antioxidants, wherein the *perilla frutescens* derived seed oil is made by subjecting the *perilla frutescens* seed to supercritical fluid CO2 extraction to produce a seed oil extract; fractionating the resulting seed oil extract in separate pressure step-down stages for collecting light and heavy fractions of seed oil extract; and separating the heavy fraction from the light fraction to form the final seed oil from the heavy fraction.

2. The composition of matter according to claim 1, wherein the selected antioxidants comprise a mixture of selected lipophilic and hydrophilic antioxidants.

3. The composition of matter according to claim 1, and further comprising lipophilic antioxidants either alone or in combination with at least one of: a) phenolic antioxidants including at least one of sage, oregano, and rosemary; b) tocopherol, c) tocotrienol(s), d) carotenoids including at least one of astaxanthin, lutein, and zeaxanthin; e) ascorbylacetate; f) ascorbylpalmitate g) Butylated hydroxytoluene (BHT); h) Docosapentaenoic Acid (BHA) or i) Tertiary Butyl hydroquinone (TBHQ).

4. The composition of matter according to claim 1, and further comprising a hydrophilic antioxidant or sequesterant comprising hydrophilic phenolic antioxidants including at least one of grape seed extract, tea extracts, ascorbic acid, citric acid, tartaric acid, and malic acid.

5. The composition of matter according to claim 1, wherein a peroxide value of the seed oil is under 10.0 meq/Km.

6. The composition of matter according to claim 1, and further comprising docosahexaenoic acid (DHA) and/or eicosapentaenoic acid (EPA) in pectin or gelatin based confectionary dietary supplement delivery systems.

7. The composition of matter according to claim 1, and further comprising EPA, DHA, docosapentaenoic acid (DPA) or gamma-linlolenic acid (GLA), fish oil, krill oil, krill oil concentrate, borage oil, evening primrose oil, olive oil or other plant, animal or algal based seed or fruit oils admixed therein.

8. The composition of matter according to claim 1, and further comprising from 85 to 95 percent w/w of PUFAs.

9. The composition of matter according to claim 1, wherein the PUFAs comprise at least greater than 56 percent alpha-linolenic acid (ALA).

10. The composition of matter according to claim 1, wherein the seed oil is shelf stable at room temperature up to 32 months.

11. The composition of matter according to claim 1, wherein said seed oil is derived from a premilled or flake-rolled cracked biomass of *perilla frutescens*.

12. A composition of matter comprising a shelf stable, supercritical, $CO^2$ fluid extracted seed oil derived from a cracked biomass of *perilla frutescens*, the seed oil comprising from 85 to 95 percent w/w of PUFAs in a ratio of from 4:1 to 6:1 alpha-linolenic acid (ALA) to linoleic acid (LA) and the PUFAs are greater than 50 percent ALA, and a mixture of selected antioxidants, including astaxanthin, phenolic antioxidants and natural tocopherols, wherein the *perilla frutescens* derived seed oil is made by subjecting the *perilla frutescens* seed to supercritical fluid CO2 extraction to produce a seed oil extract; fractionating the resulting seed oil extract in separate pressure step-down stages for collecting light and heavy fractions of seed oil extract; and separating the heavy fraction from the light fraction to form the final seed oil from the heavy fraction.

13. The composition of matter according to claim 12, comprising at least one of dispersed nano- and micro-particles of rice or sugar cane based policosanol.

14. The composition of matter according to claim 12, and further comprising lipophilic antioxidants either alone or in combination with at least one of: a) phenolic antioxidants including at least one of sage, oregano, and rosemary; b) tocopherol, c) tocotrienol(s), d) carotenoids including at least one of astaxanthin, lutein, and zeaxanthin; e) ascorbylacetate;

f) ascorbylpalmitate g) Butylated hydroxytoluene (BHT); h) Docosapentaenoic Acid (BHA) or i) Tertiary Butyl hydroquinone (TBHQ).

15. The composition of matter according to claim 12, and further comprising a hydrophilic antioxidant or sequesterant comprising hydrophilic phenolic antioxidants including at least one of grape seed extract, tea extracts, ascorbic acid, citric acid, tartaric acid, and malic acid.

16. The composition of matter according to claim 12, wherein a peroxide value of the seed oil is under 10.0 meq/Km.

17. The composition of matter according to claim 12, and further comprising docosahexaenoic acid (DHA) and/or eicosapentaenoic acid (EPA) in pectin or gelatin based confectionary dietary supplement delivery systems.

18. The composition of matter according to claim 12, and further comprising EPA, DHA, docosapentaenoic acid (DPA) or gamma-linlolenic acid (GLA), fish oil, krill oil, krill oil concentrate, borage oil, evening primrose oil, olive oil or other plant, animal or algal based seed or fruit oils admixed therein.

19. The composition of matter according to claim 12, wherein the PUFAs comprise at least greater than 56 percent alpha-linolenic acid (ALA).

20. The composition of matter according to claim 12, wherein the seed oil is shelf stable at room temperature up to 32 months.

21. The composition of matter according to claim 12, wherein said seed oil is derived from a premilled or flake-rolled cracked biomass of *perilla frutescens*.

\* \* \* \* \*